(12) United States Patent
Mosler

(10) Patent No.: US 11,109,985 B2
(45) Date of Patent: Sep. 7, 2021

(54) METHOD FOR MAKING A MOLD OF AN AMPUTATION STUMP, AND MOLDING AID FOR SUCH A METHOD

(71) Applicant: OTTO BOCK SE & CO. KGaA, Duderstadt (DE)

(72) Inventor: Luder Mosler, Duderstadt (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 106 days.

(21) Appl. No.: 16/078,337

(22) PCT Filed: Feb. 23, 2017

(86) PCT No.: PCT/EP2017/054221
§ 371 (c)(1),
(2) Date: Aug. 21, 2018

(87) PCT Pub. No.: WO2017/144604
PCT Pub. Date: Aug. 31, 2017

(65) Prior Publication Data
US 2019/0053917 A1  Feb. 21, 2019

(30) Foreign Application Priority Data
Feb. 23, 2016 (DE) .................. 202016001130.9

(51) Int. Cl.
*A61F 2/50* (2006.01)
*A61F 2/78* (2006.01)
*A61F 2/80* (2006.01)

(52) U.S. Cl.
CPC .............. *A61F 2/5046* (2013.01); *A61F 2/50* (2013.01); *A61F 2/7812* (2013.01); *A61F 2/80* (2013.01); *A61F 2002/5052* (2013.01)

(58) Field of Classification Search
CPC ........ A61F 2/50; A61F 2/5046; A61F 2/7812; A61F 2002/5052
See application file for complete search history.

(56) References Cited

U.S. PATENT DOCUMENTS

| 1,335,475 A | 3/1920 | Bergman |
| 5,432,703 A | 7/1995 | Clynch et al. |

(Continued)

FOREIGN PATENT DOCUMENTS

| EP | 0765646 A1 | 4/1997 |
| EP | 0954258 B1 | 1/2008 |

(Continued)

OTHER PUBLICATIONS

Given Limb Foundation, "Improved Casting Method for Leg Prosthetics," posted May 27, 2015, https://givenlimb.org/improved-casting-method-for-leg-prosthetics/, 3 pages.

(Continued)

*Primary Examiner* — Bruce E Snow
(74) *Attorney, Agent, or Firm* — Holland & Hart LLP

(57) ABSTRACT

A method for making a mould of an amputation stump, in which the amputation stump is inserted into a liner of a moulding aid, the liner having a longitudinal direction and a circumference, and the liner having an expansion coupling such that when the liner is extended in the longitudinal direction, this necessarily results in a reduction of the circumference.

6 Claims, 10 Drawing Sheets

(56) References Cited

U.S. PATENT DOCUMENTS

| | | | |
|---|---|---|---|
| 5,738,270 A | | 3/1998 | Becker et al. |
| 6,416,703 B1 * | | 7/2002 | Kristinsson .............. A61F 2/80 |
| | | | 264/257 |
| 7,410,350 B2 | | 8/2008 | Horiguchi et al. |
| 2010/0115757 A1 | | 5/2010 | Sacherer |
| 2013/0103166 A1 * | | 4/2013 | Butler .................. A61F 2/6607 |
| | | | 623/36 |
| 2018/0036144 A1 | | 2/2018 | Radspieler |
| 2021/0015642 A1 * | | 1/2021 | Joseph ..................... A61F 2/80 |

FOREIGN PATENT DOCUMENTS

| | | | |
|---|---|---|---|
| GB | 2188846 A | 10/1987 | |
| WO | 2008092617 A1 | 8/2008 | |
| WO | 2016135320 A1 | 9/2016 | |

OTHER PUBLICATIONS

Wu et al., "CIR Casting System for Making Transtibial Sockets," Prosthetics and Orthotics International, Mar. 2009; 33(1): pp. 1-9.
PCT International Search Report for PCT International Patent Application No. PCT/EP2017/054221, dated May 9, 2017.

* cited by examiner

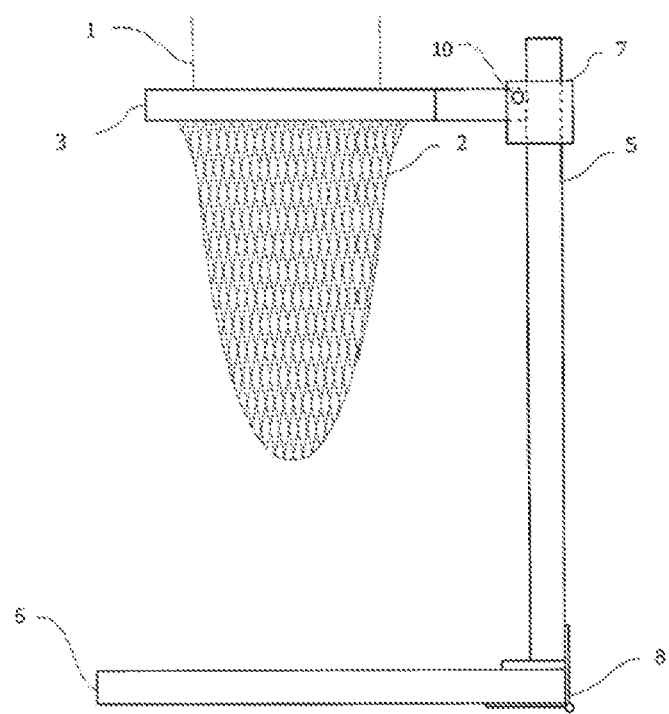

METHOD FOR MAKING A MOLD OF AN AMPUTATION STUMP, AND MOLDING AID FOR SUCH A METHOD

TECHNICAL FIELD

The invention relates to a method for making a mold of an amputation stump, in which method the amputation stump is inserted into a liner of a molding aid, said liner having a longitudinal direction and a circumference. The invention moreover relates to a molding aid for such a method.

BACKGROUND

In prosthetics of the lower extremity, the prosthesis socket assumes the crucial role of the interface to the body. Accordingly, making a mold of the amputation stump, also called the prosthetic stump, is a crucial procedure as regards the subsequent fit of the prosthesis.

Despite advances that have been made in contactless molding methods (scanning), modern practice is dominated by making a mold of the stump by means of plaster in order to create a negative of the stump. Besides the low costs, this method has the advantage that trained prosthetists can already influence the subsequent socket shape by specifically shaping the stump from plaster. This applies in particular when the subsequent socket is intended to have specific loading zones. This advantage is lost if the socket is intended to provide support over the complete surface of if inexperienced technicians carry out the molding method. There has therefore been growing interest in methods which exert uniform pressure on the stump during the molding. These include the molding method proposed by the Össur company and involving an inflated bladder, as taught in EP 0 954 258, the sand molding method developed by the Northwestern University of Chicago (Prosthetics and Orthotics International, March 2009; 33(1): 1-9), and the molding method developed by the University of Strathclyde and involving a flexible membrane in a water tank (https://givenlimb.org/improved-casting-method-for-leg-prosthetics/). The last two methods have the additional advantage that the stump can be loaded during the molding process, which results in a socket shape tailored to the loading and which can give the user an impression of the support behavior as early as the molding process.

WO 2008/092617 A1 discloses a molding aid comprising a plurality of shaped parts that are arranged to be slidable and rotatable. The shape of the stump is intended to be able to be molded thereby. A disadvantage, however, is that this cannot be done while the stump is loaded, and the shape is also not scannable by optical methods. The applicant used the "anatomical SIT-Cast" system, in which the shape of the stump was copied using a molding aid with a ring into which the stump is inserted. The stump is covered beforehand with a plaster compound and a rubber sleeve. Experience shows that this does not provide optimal loading of the stump.

A disadvantage in particular of the two last-mentioned methods is that, because of their design, they are not easily transportable and are thus of little benefit in everyday clinical practice. In all three methods, it is not possible to easily influence the result of the molding process. A combination with optical scanning methods, which are increasingly used in modern prosthetics, is likewise not possible.

WO 2016/135320 A1 discloses a device for creating a plaster impression of a limb stump, said device having a pressure vessel into which a stump, preferably covered with plaster, is inserted. A uniform pressure is intended to act on the stump through the fluid. A disadvantage, however, is that subsequent shaping of the plaster or of the stump is not possible, and the stump cannot be scanned and measured optically.

U.S. Pat. No. 7,410,350 B2 discloses a device in which an amputation stump in plaster is inserted into a container such that expander elements, which are arranged in the container, exert a pressure on the amputation stump. This is intended to overcome the disadvantages of a solution in which a plaster-coated stump is held in a ring and is loaded by the patient after an initial hardening phase in which it is not completely hardened.

SUMMARY

The problem addressed by the present invention is therefore to provide a method for making a mold of an amputation stump and a molding aid for prosthetic stumps, which exert a uniform pressure on the stump during the molding process, can preferably be loaded by the user during the molding process, are easy to handle and transport and permit direct access to the surface for the purpose of reshaping during the molding process or for optical scanning of the surface topography instead of the physical molding.

The invention solves the stated problem by providing a method for making a mold of an amputation stump, in which method the amputation stump is inserted into a liner of a molding aid, said liner having a longitudinal direction and a circumference, said method being characterized in that the liner has an expansion coupling, such that a lengthening of the liner along the longitudinal direction necessarily results in a reduction of the circumference.

A conventional liner or an elastic membrane known from the prior art is generally composed of an elastic material. When the amputation stump is located in such a material and is loaded, for example, from above in the direction of its distal end, this leads to an elastic deformation of the liner or of the membrane, mainly a lengthening along the longitudinal axis. This means that the liner or the membrane is expanded in the longitudinal axis. In the case of an elastic material, this is possible without radial forces occurring. By contrast, the liner in the molding method according to the present invention is such that a lengthening of the liner along its longitudinal axis necessarily results in a reduction of its circumference. Consequently, if the amputation stump in the liner is loaded, a lengthening of the liner along the longitudinal direction, hence also a reduction of the circumference, thus results in a force acting radially on the stump. By virtue of the particular configuration of the liner, the amputation stump is thus loaded in the radial direction uniformly and over the complete surface.

The amputation stump, after insertion into the liner, is preferably loaded by the patient. The loading causes a lengthening of the liner and, by virtue of the particular configuration of the liner, this lengthening causes a reduction of the circumference and consequently brings about a force acting radially inward on the stump. A very good loading situation of the stump during the molding process is thus achieved.

The amputation stump, prior to insertion into the liner, is preferably equipped with a molding material, for example plaster, and preferably with a release layer, in particular a release film. The molding process then takes place by the user placing the stump, coated with the molding material and optionally the release film, into the liner and exerting a tensile load on the distal end of the liner such that the liner lengthens. The placement or fitting of the stump or amputation stump into the liner can also be designated as insertion.

By means of the tensile force exerted on the end of the liner, and the coupling of the expansions of the liner, the liner now completely encloses the amputation stump and exerts a pressure on the stump in the circumferential direction, which pressure is advantageously proportional to the longitudinal loading of the liner.

Alternatively or in addition to this, the amputation stump can be measured optically after insertion into the liner. The amputation stump is preferably loaded by the patient. Here too, the above-described loading exerts tension on the distal end of the liner and thus generates a pressure on the amputation stump in the circumferential direction.

After insertion of the amputation stump into the liner, the amputation stump and/or the molding material is preferably shaped in order to obtain the advantageous effects already described.

The invention also solves the stated problem by providing a molding aid for a method described here. This molding aid therefore has the above-described liner with the described expansion coupling. The liner advantageously has or is made of a braided tube or a net of preferably intersecting fibers. The fibers, in an unloaded state of the liner, advantageously run at an angle of 45° to the longitudinal direction of the liner. This is called a diagonal fiber run. An exact angle of 45° is not necessary, as long as the desired coupling between the longitudinal expansion and the reduction of the circumference is achieved. The force exerted on the amputation stump, and caused by a lengthening of the liner along its longitudinal direction, can be adjusted via the angle between the fiber run and the longitudinal direction of the liner. The flatter the fiber run, i.e. the closer the described angle comes to a right angle, the greater the radially directed force that occurs during loading along the longitudinal direction.

The liner is advantageously held in a retaining device, preferably a securing ring. In a preferred embodiment, the liner is held in a ring shape at its proximal end.

In order to permit the greatest possible freedom of orientation of the amputation stump, the retaining device, in particular the proximal securing ring, is mounted such that there is a uniform longitudinal force on the entire circumference of the liner. Various solutions are conceivable for this purpose:

The securing ring can be cardanically mounted.
The securing ring can have a spherical support which is mounted in a correspondingly shaped ring.
The securing ring can be mounted on at least two angled links or leaf springs which, on account of their multi-articulation kinematics, permit a pivoting movement of the securing ring.
The securing ring can permit tautening of the liner in the fitting process, such that the liner can align itself according to the orientation of the stump and, according to the fixing at the proximal edge, follows the orientation of the stump.

The retaining device is preferably adjustable in height. It is thus possible, in a particularly simple way, to deal with different heights of patients and different lengths of amputation stumps.

For this purpose, a variable clamping device is advantageously provided for the proximal edge of the liner. In this preferred, particularly simple solution, the liner can be turned back at the proximal end around a loose ring, in order then to be guided distally within the securing ring. By pulling on the liner edge in the distal direction, the liner can be brought to bear on the stump while the user is standing on one leg. Through the two-fold deflection of the liner, the latter is fixed in the securing ring and can be loaded by the user.

The liner is preferably deflected about a ring and guided back onto itself, wherein the ring with the liner comes to bear on a retaining device. This particularly simple way of securing the liner permits a structurally simple molding aid that is therefore cost-effective to produce. The retaining device is advantageously secured on a support device, for example a column, and is advantageously pivotable. In this way, the retaining device can advantageously be pivoted about the longitudinal direction of the support device.

In a preferred embodiment, the retaining device is arranged to be foldable on the support device. In this way, it can be brought to a position of use, in which the patient can insert his amputation stump into a liner arranged in the retaining device, and to a transport position, in which the retaining device is for example folded onto the support device in order to reduce the required installation space. In particular in one of these positions, advantageously in a folded down position corresponding to the position of use, the retaining device advantageously engages in latching elements, preferably latches of the support device, or is clamped or wedged onto the support device. In this way, sufficient stability is achieved and incorrect use is virtually excluded.

The support device, i.e. in particular the securing ring, should be mounted such that good access is possible for a prosthetist. At the same time, the support device is advantageously adjustable in height and exchangeable. In this way, it is possible, for example, to use different sizes of a securing ring. In order to permit easy transport, it is helpful if the entire molding aid can be folded together, for example in order to be easily stowed in a workshop and to be transportable in everyday clinical practice. In a preferred embodiment of the invention, the retaining device, in particular the securing ring, is therefore secured in a foldable manner on a vertical column. For this purpose, for example, a hinge and a fastenable clip can be provided around the column. In a preferred solution, the retaining device generates the forces to lock itself, by means of the securing ring being loaded. For this purpose, the securing ring, when folded down, can engage for example in latches in the column. With a corresponding configuration, it is also possible to generate the locking only by frictional forces, which permits a stepless height adjustment. Similarly, the column of the molding aid can be configured such that, for storage and transport, it can be released from its securing for example on a base plate. For this purpose, a releasable connection, for example a plug connection, can be provided. In a further preferred embodiment, the column is connected to the base plate via a hinge. It can be pivoted to the desired position. The working position of the column preferably forms the abutment for such a pivoting movement, such that the column adopts a stable, preferably vertical position during the molding process. For storage or transport, it can be pivoted, for example, toward the base plate.

The liner, which is in particular produced from a liner material, preferably has a plurality of fibers which are arranged in the liner material. These fibers are preferably composed of a non-elastic material. The liner can have several fiber plies, preferably two, which have a plurality of fibers advantageously extending parallel to each other at least in one region in each fiber ply. As long as the fibers of the different fiber plies intersect each other, the desired effect of the coupling of the expansions can also be achieved in this way.

Additionally or alternatively to this, the fibers can also form a spiral-shaped matrix. The liner then has first fibers, which form a spiral-shaped matrix in a first circumferential direction, and second fibers, which form a spiral-shaped matrix in a second circumferential direction counter to the first circumferential direction. Spiral-shaped in this case means that the respective fibers extend in preferably several windings about the circumference of the amputation stump and therefore of the liner, when the liner bears on the amputation stump.

The fibers arranged in the liner material advantageously intersect at a right angle. This applies in particular when no amputation stump is located in the liner. This angle can be changed by the insertion of the stump and in particular by the load.

Of course, the liner can also be composed of several partial liners which each have only one fiber ply with only one fiber direction. As an alternative to intersecting fibers, it is also possible, for example, for hexagonal nets made of non-elastic fibers to be embedded in the liner material. Of course, other nets that have the desired properties are also possible. This means that a lengthening of the net in one direction necessarily leads to a shortening of the net in the other direction.

BRIEF DESCRIPTION OF THE DRAWINGS

Illustrative embodiments of the present invention are explained in more detail below with reference to the attached drawings, in which:

FIG. 3 shows the schematic view of a molding aid with the amputation stump inserted;

DETAILED DESCRIPTION

Figure 1A:
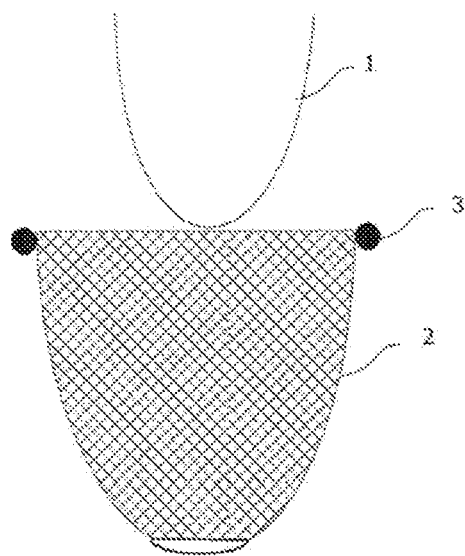
FIGS. 1a and 1b show schematic views of a liner and of an amputation stump before and after insertion.
Figure 1B:
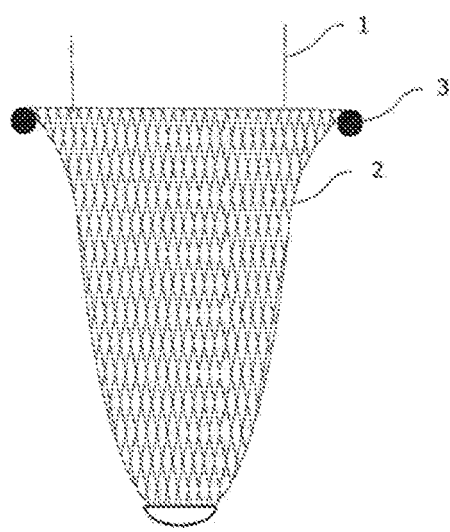

FIG. 1 shows schematically the function of the coupling of longitudinal and transverse expansion in the liner (2), while the prosthetic stump is being received. The prosthetic stump is secured on the securing ring (3) and, as is indicated in the surface texture, is made of a net or braid with diagonally extending fiber orientation. By longitudinal deformation of the liner, there is an increased orientation of the fibers in the longitudinal direction, which at the same time reduces the circumference of the liner. The deformation of the liner ceases when the stump (1) is completely enclosed. When the stump is subjected to a load, a uniform pressure is exerted on the stump. The liner consists of a braided tube of yarn or monofilaments or of a net of tubular shape with a diagonal profile of the filaments or with a hexagonal structure. Braided tubes made of polyamide or polypropylene monofilaments are particularly advantageous, since these are very movable and yet form a closed surface. The size is chosen such that the stump is completely enclosed when the filaments of the braided tube have an intersection angle of approximately 90° or when the hexagonal structure is undistorted. At the distal end, the tube can be bound together or adhesively bonded or welded to a flexible closure cap (9). In any case, it is recommended to generate a smooth surface internally at the distal end by means of an elastic plate being bonded in or by means of the distal end being cast with elastomer. At the proximal end, the liner is connected to the securing ring (3).

Figure 2A:
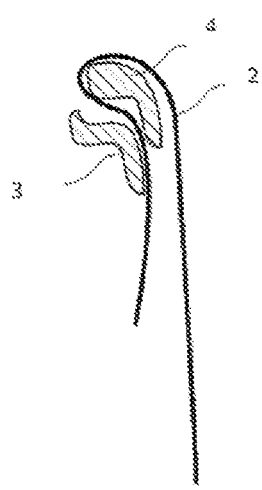
FIGS. 2a and 2b show schematic drawings illustrating the way in which the liner is secured.
Figure 2B:
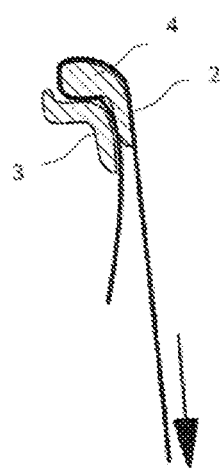

FIG. 2 shows a cross-sectional view of an advantageous securing of the liner on the securing ring (3). The securing ring (3) can have a stepped configuration in order to provide centering for the ring (4). The liner (2) is folded about the ring (4) and guided back onto itself within the securing ring (3). When the liner is subjected to a load, as shown in FIG. 2B, the multiple deflection results in the ring (4) being pressed firmly onto the securing ring (3), consequently with high frictional forces which hold the liner safely in the securing ring as long as it is loaded. An advantage of this arrangement is that the liner can be oriented inside the ring according to the position of the lower limb. Ideally, the liner is fitted by being held taut on the stump, when the folded-down end is pulled, and then being subjected to a load by the user.

FIG. 3 shows a possible embodiment of the whole molding aid. The liner (2) receives the stump (1). Its proximal end is held in the securing ring (3). The latter is secured on the column (5) by means of a clip (7). The axle (10) allows the securing ring (3) to be folded up onto the column. When folded down, the configuration creates an abutment which holds the securing ring in a horizontal position. At the same time, when the securing ring is loaded from above, strong forces act on the column and prevent the clip from slipping along the column. In this way, the securing ring (3) is steplessly adjustable in height, without a lock having to be released for this purpose. The column (5) is secured on the base plate (6) by means of a hinge. In the vertical position of the column, the position of the rotation point of the hinge creates an abutment, which is stabilized by the securing ring (3) being loaded from above. It is thus possible for the molding aid to be used without danger of the column pivoting rearward.

Figure 4:
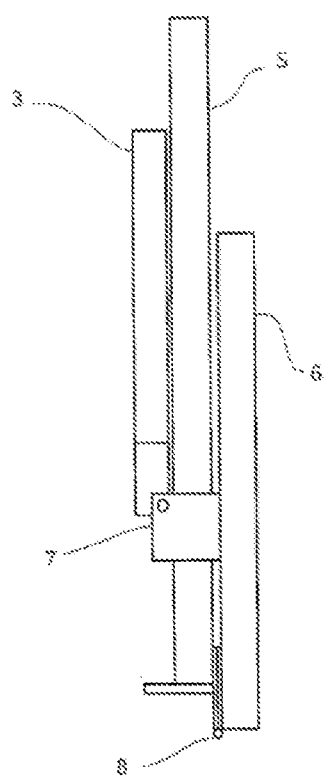
FIG. 4 shows the schematic view of a molding aid in the transport position.

FIG. 4 shows the molding aid from FIG. 3 in the folded-up state. The column (5) is here pivoted onto the underside of the base plate (6). The securing ring (3) is folded against the column (5). It can be seen that the molding aid is very compact in this state and can be easily transported and stowed. Its erection requires few maneuvers.

Figure 5:
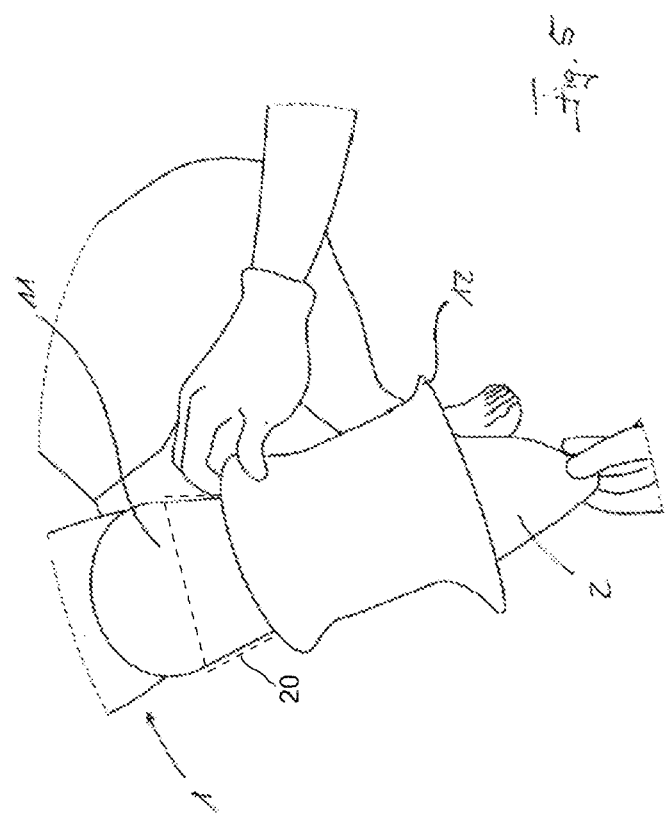
FIGS. 5 to 8 show various stages of a molding method according to an illustrative embodiment of the present invention.

FIG. 5 shows how the amputation stump 1, which in the illustrative embodiment shown is equipped with a modeling layer of plaster 11 and a release film 20, is inserted into the liner 2. A distal edge 12 of the liner 2 is turned back. The individual fibers, through which the coupling between longitudinal expansion and circumferential reduction is obtained in the illustrated liner 2, are not shown in FIGS. 5 to 10.

Figure 6:
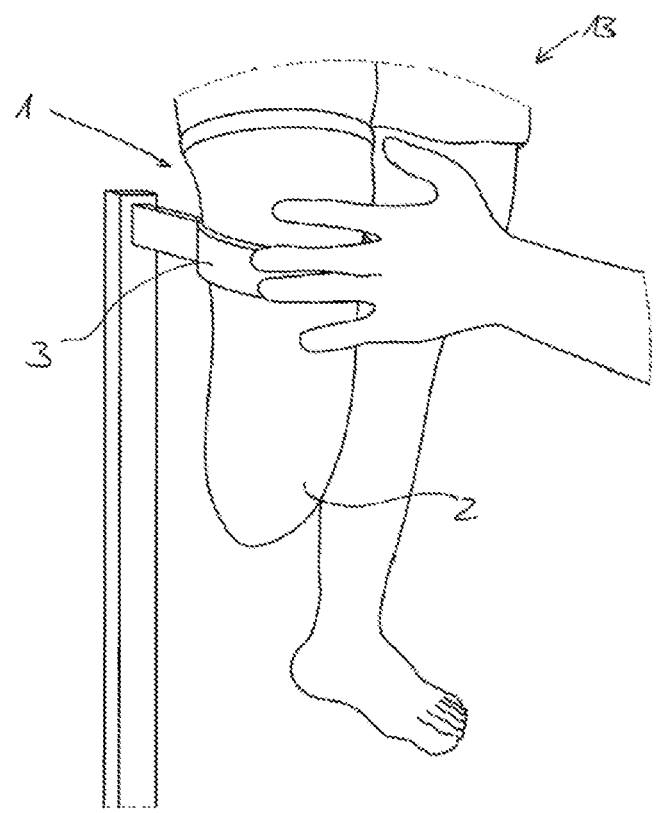

The following is shown in FIG. 6. The patient 13 stands on his intact leg, and the stump 1 with the liner 2 is inserted into the securing ring 3 and is held there. The patient 13 can now exert a load on the amputation stump 1 and thereby ensures that the liner 2 is lengthened in the longitudinal direction, i.e. from the top downward in FIG. 6. By means of the coupling between longitudinal expansion and transverse expansion, this necessarily leads to a reduction of the circumference and therefore to a force that acts on the amputation stump 1 and is directed radially inward.

Figure 7:
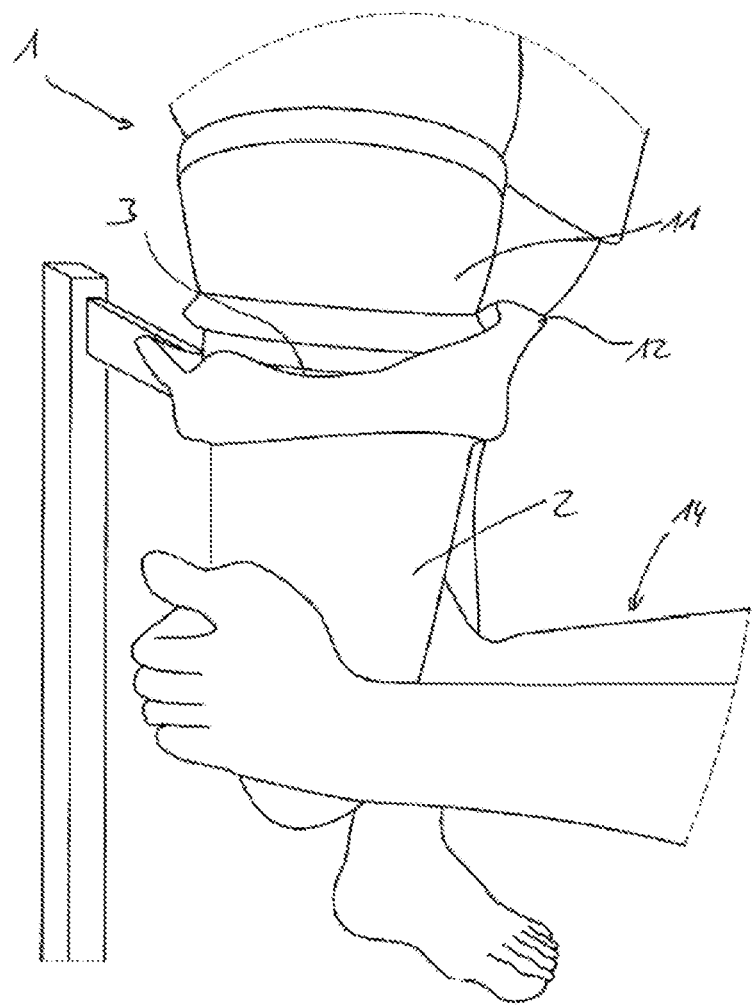

The situation from FIG. 6 is again shown in FIG. 7, where a further person, for example a prosthetist 14, is now able to shape the amputation stump 1 in the liner 2 while the amputation stump 1 is held in the securing ring 3. In this way, the layer of plaster 11, which is located inside the liner 2, can be modeled and, if appropriate, shaped or reshaped. In this way, account can be taken of the individual circumstances presented by the amputation stump 1.

Figure 8:
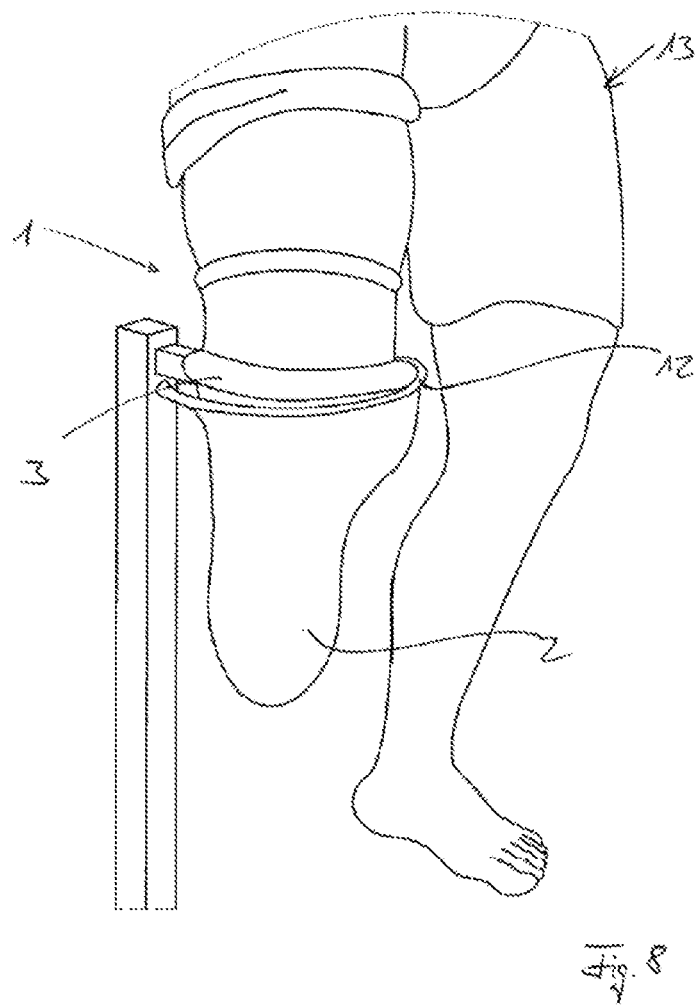

FIG. 8 shows the concluding phase, in which the patient 13 stands on his intact leg and exerts a load on the amputation stump 1 inside the securing ring 3. In this way, the already described force is applied by the liner 2 to the amputation stump and the molding material of plaster 11 which is located inside the liner, until the material is sufficiently hardened to remove the liner from the securing ring 3.

Figure 9:
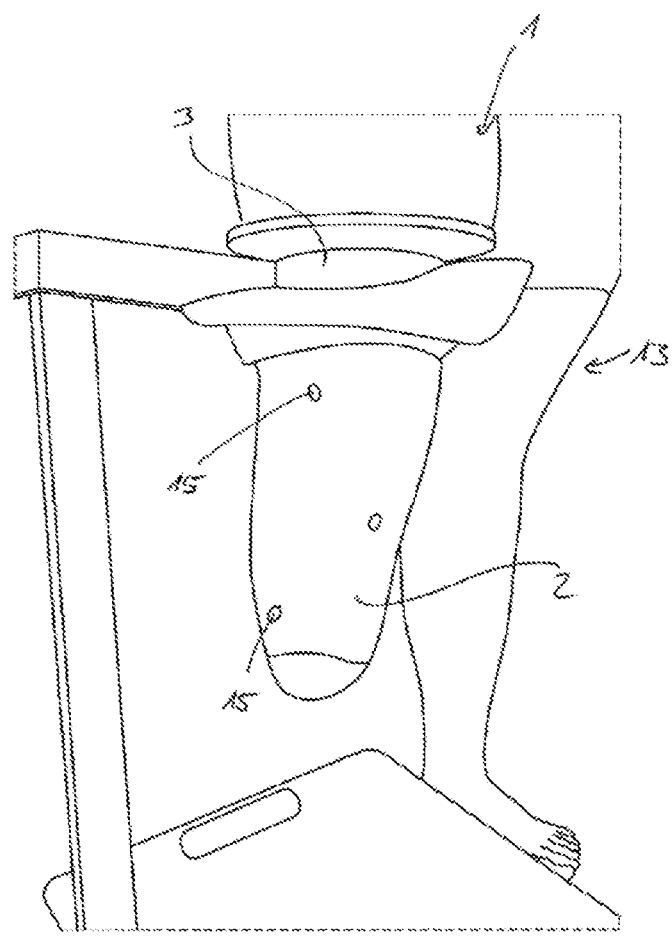
FIGS. 9 and 10 show two depictions of different stages of a method according to a further illustrative embodiment of the present invention.

FIG. 9 shows the situation in a method according to a further illustrative embodiment of the present invention. The patient 13 again stands on his intact leg, and the amputation stump 1 is inserted into the liner 2. However, in contrast to FIGS. 5 to 8, there is no plaster 11 arranged inside the liner between the liner 2 and the amputation stump 1. The liner is again held in the securing ring 3, but it now has markings 15 which permit an optical measurement.

Figure 10:
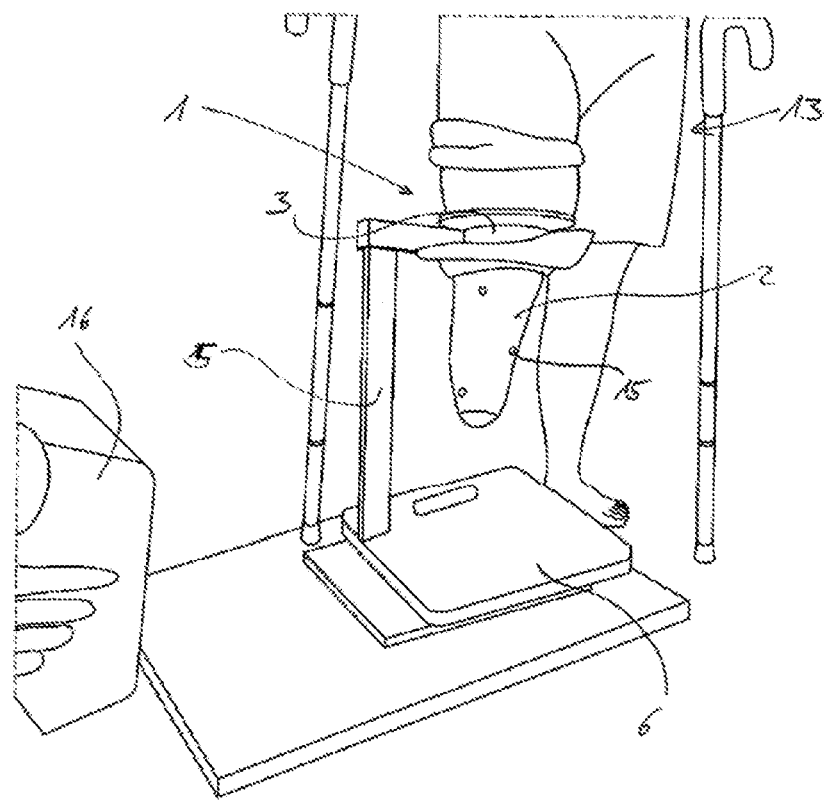

This optical measurement is shown in FIG. 10. The amputation stump 1 of the patient 13 is located in the liner 2, which has the configuration shown in FIG. 9. By means of a laser measurement device 16, as is known in principle from the prior art, the geometric shape of the liner 2 in which the amputation stump 1 is located is now measured three-dimensionally. The data thus determined can be used to produce the prosthesis socket. The securing ring 3 is arranged on the column 5 and is preferably adjustable in height, i.e. displaceable in particular along the longitudinal direction of the column. In a particularly preferred embodiment, the securing ring 3 is additionally pivotable toward the column 5 in order to be able to bring the molding aid to the transport position shown in FIG. 5. For this purpose, it is advantageous if the base plate 6 is also pivotable relative to the column 5.

LIST OF REFERENCE SIGNS 1 stump
2 liner
3 securing ring
4 ring
5 column
6 base plate
7 clip
8 hinge
9 closure cap
10 axle
11 plaster
12 distal edge
13 patient
14 prosthetist
15 marking
16 laser measurement device

The invention claimed is:

1. A method for making a mold of an amputation stump, the method comprising:
    inserting the amputation stump into a liner of a molding aid, the liner having a longitudinal direction, a circumference, and an expansion coupling;
    positioning a molding material between the liner and the amputation stump;
    positioning a release layer or release film between the liner and the molding material;
    lengthening the liner along the longitudinal direction after insertion of the amputation stump to reduce the circumference and shape the molding material.

2. The method as claimed in claim 1, wherein the amputation stump, after insertion into the liner, is loaded by the patient to lengthen the liner.

3. The method as claimed in claim 1, wherein the amputation stump, prior to insertion into the liner, is equipped with the molding material and the release layer or release film.

4. The method as claimed in claim 3, wherein after insertion of the amputation stump into the liner, shaping at least one of the amputation stump and the molding material.

5. The method as claimed in claim 1, wherein the amputation stump is measured optically after insertion into the liner.

6. The method as claimed in claim 1, wherein the liner is separable from the molding material.

* * * * *